United States Patent
Cahan et al.

(10) Patent No.: US 10,611,994 B2
(45) Date of Patent: Apr. 7, 2020

(54) ELECTROCHEMICAL SENSORS FOR CELL CULTURE MONITORING

(71) Applicant: INTERNATIONAL BUSINESS MACHINES CORPORATION, Armonk, NY (US)

(72) Inventors: Amos Cahan, Dobbs Ferry, NY (US); Guy M. Cohen, Ossining, NY (US); Theodore G. van Kessel, Millbrook, NY (US); Sufi Zafar, Briarcliff Manor, NY (US)

(73) Assignee: International Business Machines Corporation, Armonk, NY (US)

( * ) Notice: Subject to any disclaimer, the term of this patent is extended or adjusted under 35 U.S.C. 154(b) by 284 days.

(21) Appl. No.: 15/251,215

(22) Filed: Aug. 30, 2016

(65) Prior Publication Data

US 2018/0057785 A1     Mar. 1, 2018

(51) Int. Cl.
| | |
|---|---|
| *G01N 33/483* | (2006.01) |
| *C12M 1/34* | (2006.01) |
| *C12M 1/00* | (2006.01) |
| *C12M 1/36* | (2006.01) |

(52) U.S. Cl.
CPC ............ *C12M 41/46* (2013.01); *C12M 23/28* (2013.01); *C12M 41/32* (2013.01); *C12M 41/36* (2013.01); *C12M 41/48* (2013.01); *G01N 33/4836* (2013.01)

(58) Field of Classification Search
CPC ...... C12M 41/46; C12M 41/32; C12M 41/36; C12M 41/48; C12M 41/26; C12M 41/28; C12M 41/30; C12M 23/28; G01N 33/0009; G01N 33/0031; G01N 33/0036; G01N 33/0062; G01N 33/0068; G01N 33/4836; G01N 33/48
See application file for complete search history.

(56) References Cited

U.S. PATENT DOCUMENTS

| | | | |
|---|---|---|---|
| 7,919,319 | B2 | 4/2011 | Jervis et al. |
| 7,948,015 | B2 | 5/2011 | Rothberg et al. |
| 8,262,900 | B2 | 9/2012 | Rothberg et al. |

(Continued)

FOREIGN PATENT DOCUMENTS

| | | |
|---|---|---|
| CN | 103472114 B | 5/2015 |
| DE | 10 2014 218 298 A1 | 3/2016 |

(Continued)

OTHER PUBLICATIONS

Bates, J.B. et al., "Thin-film lithium and lithium-ion batteries" Solid State Ionics (2000) pp. 33-45, vol. 135.

*Primary Examiner* — Susan D Leong
(74) *Attorney, Agent, or Firm* — Tutunjian & Bitetto, P.C.; Vazken Alexanian

(57) ABSTRACT

A device for monitoring a cell culture includes one or more electrochemical sensors configured to be positioned adjacent to or embedded within a medium of a cell culture. The one or more electrochemical sensors are configured to generate signals in accordance with the cell culture. A data storage device is configured to receive and store the signals from the one or more electrochemical sensors. A computation device is configured to analyze the signals from the one or more electrochemical sensors to determine cell activity over time using sensitivity information.

10 Claims, 9 Drawing Sheets

(56) References Cited

U.S. PATENT DOCUMENTS

| | | |
|---|---|---|
| 8,306,757 B2 | 11/2012 | Rothberg et al. |
| 8,333,874 B2 | 12/2012 | Currie |
| 8,921,093 B2 | 12/2014 | Seitz et al. |
| 8,957,687 B2 | 2/2015 | Nackaerts et al. |
| 9,134,269 B2 | 9/2015 | Rothberg et al. |
| 9,194,000 B2 | 11/2015 | Rothberg et al. |
| 9,269,708 B2 | 2/2016 | Rothberg et al. |
| 2007/0161106 A1* | 7/2007 | Jervis .................... C12M 23/16 435/325 |
| 2012/0223217 A1* | 9/2012 | Zheng .................... B01L 3/508 250/215 |
| 2013/0109048 A1* | 5/2013 | Giugliano .......... G01N 33/4836 435/29 |
| 2013/0209991 A1* | 8/2013 | Wang .................. A61B 5/1473 435/5 |
| 2001/5011870 | 4/2015 | Selvaganapathy |
| 2015/0330941 A1* | 11/2015 | Smith ............... H01L 29/66969 257/253 |
| 2018/0321184 A1* | 11/2018 | Mackin .............. G01N 27/4146 |

FOREIGN PATENT DOCUMENTS

| | | |
|---|---|---|
| JP | 2015-508895 A | 3/2015 |
| KR | 10-2015-0013128 A | 2/2015 |
| WO | 2015/050225 A1 | 4/2015 |
| WO | 2016/036410 A1 | 3/2016 |

\* cited by examiner

ELECTROCHEMICAL SENSORS FOR CELL CULTURE MONITORING

BACKGROUND

Technical Field

The present invention generally relates to cell sensors, and more particularly to devices and methods for sensing cell activity using electrochemical feedback.

Description of the Related Art

Cells are commonly grown in a lab on dishes or in wells that contain nutrients in the form of fluid, gel or solids. These may be human or animal cells, as well as microorganisms, such as bacteria, fungi, archaea and eukaryotic parasites used in research or clinical diagnostics and therapeutics. Cells are typically grown in an incubator with controlled temperature and humidity. To determine the degree of growth of cells, the cells are most often monitored visually by a human. For example, samples from potential infection sites in patients are inoculated on a Petri dish and a lab technician may visually inspect the dish after a few hours to a few days to spot signs of bacterial colony formation. This is labor intensive and also is associated with a risk for contamination. When cells require a strict anaerobic environment, visually inspecting the cells entails exposing them (even if for a limited period of time) to air, which may delay their growth or lead to their death.

Visual inspection is widely used to determine bacterial susceptibility to antibiotics, for example, using a disc-diffusion test, wherein bacterial growth is inhibited around a disc containing an antibiotic drug. However, it is practically impossible for humans to continuously monitor cells in a culture. Moreover, for microorganism growth to be visually evident to the naked eye takes an extremely high number of cells to be accumulated.

SUMMARY

In accordance with an embodiment of the present invention, a device for monitoring a cell culture includes one or more electrochemical sensors configured to be positioned adjacent to or embedded within a medium of a cell culture. The one or more electrochemical sensors are configured to generate signals in accordance with the cell culture. A data storage device is configured to receive and store the signals from the one or more electrochemical sensors. A computation device is configured to analyze the signals from the one or more electrochemical sensors to determine cell activity over time using sensitivity information.

Another device for monitoring a cell culture includes a semiconductor substrate having source and drain regions formed therein and a gate conductor being disposed between the source and drain regions to form transistors that function as electrochemical sensors. A sensing layer is configured to interact with a cell culture in a medium. A reference electrode disposed within the medium and configured to activate the electrochemical sensors positioned adjacent to or embedded within the medium of the cell culture, the one or more electrochemical sensors configured to generate signals in accordance with the cell culture. In one embodiment, the sensing layer includes a gate dielectric, and the gate conductor includes the medium being measured.

A method for monitoring a cell culture includes positioning one or more electrochemical sensors adjacent to or embedded within a medium of a cell culture; generating signals in accordance with the cell culture; and analyzing the signals from the one or more electrochemical sensors to determine cell activity over time using sensitivity information.

These and other features and advantages will become apparent from the following detailed description of illustrative embodiments thereof, which is to be read in connection with the accompanying drawings.

BRIEF DESCRIPTION OF THE SEVERAL VIEWS OF THE DRAWINGS

The disclosure will provide details in the following description of preferred embodiments with reference to the following figures wherein.

DETAILED DESCRIPTION

Figure 1:
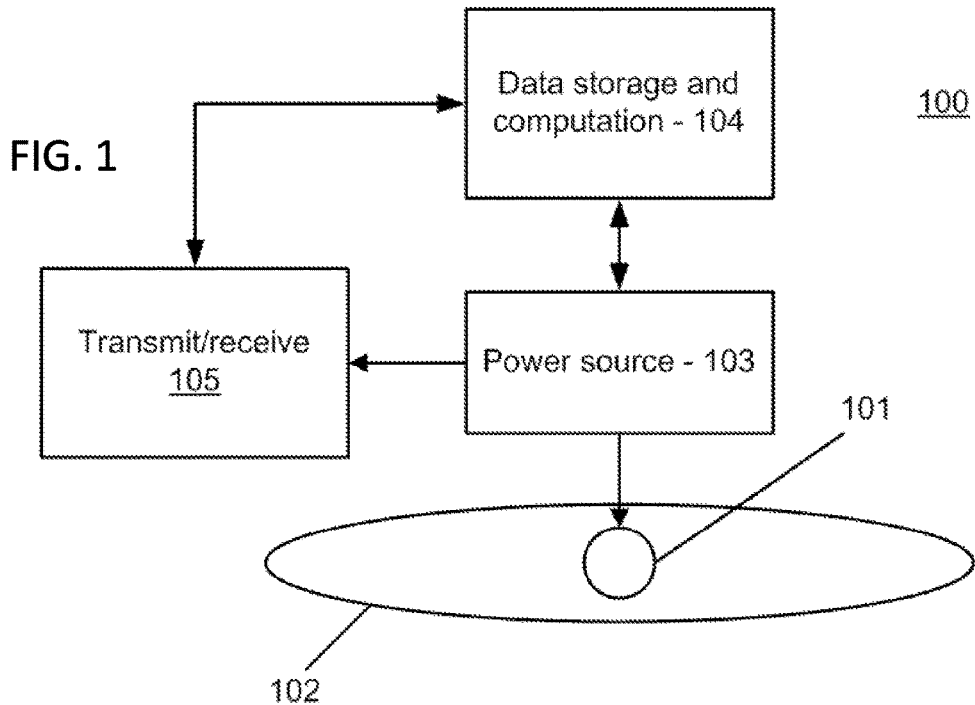
FIG. 1 is a block/flow diagram showing a device/method for monitoring electrochemical signals in a cell culture in accordance with one embodiment.

In accordance with the present principles, cell metabolism, viability and growth in culture are monitored. In one embodiment, thin electrochemical sensors are embedded in a culture medium to monitor cell metabolism viability and growth in culture through measurement of pH, electric current, ion and biomolecule concentration, etc. In a useful embodiment, an apparatus for monitoring a cell culture includes one or more electrochemical sensors positioned adjacent to a cell culture or embedded within a cell culture medium, the one or more electrochemical sensors are capable of recording an electrochemical signal from the cell culture. A power source is provided in electrical communication with the one or more electrochemical sensors. A data storage and computation device is configured to receive and analyze the electrochemical signal from the one or more electrochemical sensors. A transmitter device may be provided in electrical communication with the storage and computation device so that a pattern of viability, metabolism and growth in the cell culture can be monitored.

In another embodiment, methods for monitoring and analyzing the viability, growth and metabolic activity of cells include recording one or more signal streams from electrochemical sensors that are adjunct to or embedded within a cell-culture medium and analyzing the signals by a computerized process to determine different measurements. The measurements may include, e.g., intensity of metabolism in the cells, consumption of nutrients from the cell culture medium; rate of accumulation of waste products of cell metabolism; temperature; pH; electric current, etc. Sensing may permit for comparison between different regions within the cell culture and assess dynamics in signal patterns over time and optionally correct the analysis by comparing the signals of the cells with reference signals obtained from other cell cultures to provide a corrected analysis.

The methods and systems described herein provide for real time monitoring of cell cultures. The real-time monitoring enables a determination of the viability of cells, their metabolic activity, and the effect of drugs or changing growth conditions on their metabolism or viability. This provides timely detection of bacterial, archaeal and eukaryotic cells (including fungal and parasitic growth), particularly in clinical samples taken in case of suspected infection, before colonies are visible to the naked eye. This also shortens the time needed to determine antibiotic susceptibility by detecting change of growth in the presence of different antibiotics at different concentrations and enables the monitoring of cells grown in anaerobic conditions without the need to expose cells to air to visually examine them. In addition, cancer cells can be differentiated from normal cells by detecting differences in their metabolism or growth pattern, and the susceptibility of cancer cells to anti-neoplastic treatments (including chemical and biologic agents or ionizing radiation) in-vitro can be evaluated.

The continuous monitoring and increased sensitivity can be employed to facilitate academic research by allowing low cost real-time monitoring of growing cells, which can provide indications on the effects of genetic and other manipulations on cells or environmental conditions and provide early detection of cell culture contamination or inappropriate ambient environments through unexpected changes in metabolism or viability.

In some embodiments, systems or devices detect electrochemical signals resulting from metabolic activity in cells grown in culture. The systems may include one or more electrochemical sensors, a power source, wireless or wired communication to a digital storage and a computation device to analyze data recorded by the electrochemical sensors. This information is communicated to a user. The electrochemical sensors are placed adjunct to a surface on which cells are grown or embedded within cell culture medium. Electrochemical sensors provide signal streams from at least a part of the monitored surface. A sampling frequency of electrochemical sensors may vary from continuous to intermittent. Electrochemical sensors may monitor similar surfaces which are cell-free (control) or on which cells grow in a reference setting to correct for noise. Spatiotemporal changes in signal are recorded and analyzed by a computer connected to the electrochemical sensors or remotely.

Analysis of signals generated by electrochemical sensors allows for identification of locations in which signals indicate higher or lower metabolic activity. When employed on bacterial cell cultures, the system may support detection of early stage bacterial growth, estimation of the inoculum, prediction of the type of microorganism(s) growing by the spatial pattern of growth and the growth rate. A similar approach may be applied to cultures of archaea, fungi, amoeba and other eukaryotic cell types.

The present principles may be applied to any cell culture for measuring the consumption of nutrients, generation of cellular waste products identification of metabolic responses to interventions (such as exposing cells to a drug, change in nutrients provided, change in ambient conditions or manipulating gene expression), as well as early detection of malfunction of cells due to a disease (e.g., contamination of the culture or infection with a bacterium, phage, virus or fungus) or to implausible ambient conditions. Monitoring electrochemical sensors can potentially add to the ability to differentiate healthy from sick tissues sampled from a human or animal body.

It is to be understood that the present invention will be described in terms of a given illustrative architecture; however, other architectures, structures, substrate materials and process features and steps may be varied within the scope of the present invention.

It will also be understood that when an element such as a layer, region or substrate is referred to as being "on" or "over" another element, it can be directly on the other element or intervening elements may also be present. In contrast, when an element is referred to as being "directly on" or "directly over" another element, there are no intervening elements present. It will also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

The present embodiments may include a design for an integrated circuit chip, which may be created in a graphical computer programming language, and stored in a computer storage medium (such as a disk, tape, physical hard drive, or virtual hard drive such as in a storage access network). If the designer does not fabricate chips or the photolithographic masks used to fabricate chips, the designer may transmit the resulting design by physical means (e.g., by providing a copy of the storage medium storing the design) or electronically (e.g., through the Internet) to such entities, directly or indirectly. The stored design is then converted into the appropriate format (e.g., GDSII) for the fabrication of photolithographic masks, which typically include multiple copies of the chip design in question that are to be formed on a wafer. The photolithographic masks are utilized to define areas of the wafer (and/or the layers thereon) to be etched or otherwise processed.

Methods as described herein may be used in the fabrication of integrated circuit chips. The resulting integrated circuit chips can be distributed by the fabricator in raw wafer form (that is, as a single wafer that has multiple unpackaged chips), as a bare die, or in a packaged form. In the latter case, the chip is mounted in a single chip package (such as a plastic carrier, with leads that are affixed to a motherboard or other higher level carrier) or in a multichip package (such as a ceramic carrier that has either or both surface interconnections or buried interconnections). In any case, the chip is then integrated with other chips, discrete circuit elements, and/or other signal processing devices as part of either (a) an intermediate product, such as a motherboard, or (b) an end product. The end product can be any product that includes integrated circuit chips, ranging from toys and other low-end applications to advanced computer products having a display, a keyboard or other input device, and a central processor.

It should also be understood that material compounds will be described in terms of listed elements, e.g., SiGe. These compounds include different proportions of the elements within the compound, e.g., SiGe includes $Si_xGe_{1-x}$ where x is less than or equal to 1, etc. In addition, other elements may be included in the compound and still function in accordance with the present principles. The compounds with additional elements will be referred to herein as alloys.

Reference in the specification to "one embodiment" or "an embodiment" of the present principles, as well as other variations thereof, means that a particular feature, structure, characteristic, and so forth described in connection with the embodiment is included in at least one embodiment of the present principles. Thus, the appearances of the phrase "in one embodiment" or "in an embodiment", as well any other variations, appearing in various places throughout the specification are not necessarily all referring to the same embodiment.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This may be extended, as readily apparent by one of ordinary skill in this and related arts, for as many items listed.

The terminology used herein is for the purpose of describing particular embodiments only and is not intended to be limiting of example embodiments. As used herein, the singular forms "a," "an" and "the" are intended to include the plural forms as well, unless the context clearly indicates otherwise. It will be further understood that the terms "comprises," "comprising," "includes" and/or "including," when used herein, specify the presence of stated features, integers, steps, operations, elements and/or components, but do not preclude the presence or addition of one or more other features, integers, steps, operations, elements, components and/or groups thereof.

Spatially relative terms, such as "beneath," "below," "lower," "above," "upper," and the like, may be used herein for ease of description to describe one element's or feature's relationship to another element(s) or feature(s) as illustrated in the FIGS. It will be understood that the spatially relative terms are intended to encompass different orientations of the device in use or operation in addition to the orientation depicted in the FIGS. For example, if the device in the FIGS. is turned over, elements described as "below" or "beneath" other elements or features would then be oriented "above" the other elements or features. Thus, the term "below" can encompass both an orientation of above and below. The device may be otherwise oriented (rotated 90 degrees or at other orientations), and the spatially relative descriptors used herein may be interpreted accordingly. In addition, it will also be understood that when a layer is referred to as being "between" two layers, it can be the only layer between the two layers, or one or more intervening layers may also be present.

It will be understood that, although the terms first, second, etc. may be used herein to describe various elements, these elements should not be limited by these terms. These terms are only used to distinguish one element from another element. Thus, a first element discussed below could be termed a second element without departing from the scope of the present concept.

Referring now to the drawings in which like numerals represent the same or similar elements and initially to FIG. 1, an apparatus 100 is illustratively shown for monitoring electrochemical signals in a cell culture. The apparatus 100 includes one or more electrochemical sensors 101 positioned adjacent to, on top of, or embedded within a cell culture medium 102 on which cells are grown. A power source 103 provides power to the electrochemical sensors 101. The power source 103 may include a portable source, such as a battery or may include a photosensor or other device or may include a plug-in source (for a power grid, etc.). A data storage and computation device 104 is configured to receive and analyze the electrochemical signals from the sensors 101. The data storage and computation device 104 may be remotely located or locally located but at a different location than the medium 102 and the sensors 101. A transmitter/receiver device 105 may be connected to the storage and computation device 104 to send and receive signals, commands, data, etc. between components, e.g., sensors 101 or to a remote reporting devices, etc.

In one embodiment, the data storage and computation device 104 may be configured on a same chip or board or may include separate devices. In one embodiment, the data storage and computation device 104 includes an application specific integrated circuit (ASIC) having a processor and memory storage. The processor interrogates the sensors 101, controls sample frequency and distributes data measurements from the sensors 101 to the memory storage for present or future reference. The memory may include a solid state memory, registers, buffers, etc. for storing the data measurements from the sensors 101.

The apparatus or devices as described herein may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 2:
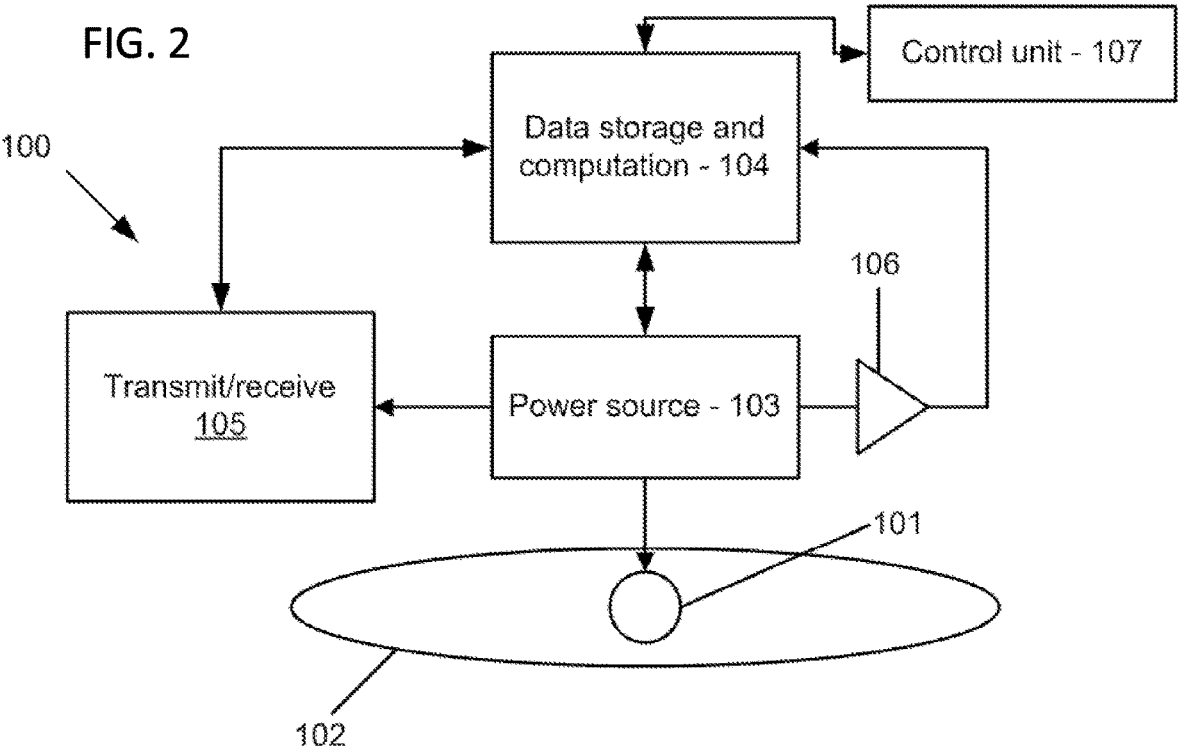
FIG. 2 is a block/flow diagram showing a device/method for monitoring electrochemical signals in a cell culture having a control unit to receive information from other components in accordance with one embodiment.

Referring to FIG. 2, in another embodiment, a control unit 107 may be coupled to the apparatus 100 to receive information from components of the apparatus 100. The control unit 107 can be any computation device, such as, e.g., a smartphone, laptop, cloud or network service device, a computer or any other computation device. The control unit 107 can receive electrochemical signal information from the sensors 101 or from the transmit/receive device 105, and can analyze and process the information to produce a determination of cell environment, cell viability, metabolism or growth in the cell culture. In some embodiments, the control unit 107 is in communication with the data storage and computation device 104. In some embodiments, the functions of transmit/receive device 105 and data storage and computation device 104 are incorporated into the control unit 107. In other embodiments, the control unit 107 produces an analysis of metabolic activity of the cell culture over time. The control unit 107 in such an embodiment receives data from the electrochemical sensors 101, analyzes it, and then processes it to produce a determination of environmental parameters and measures of metabolic activity in the cell culture.

The control unit 107 may employ its other functionality to alert users in the vicinity or over a network (e.g., wired, wireless or cellular network) of the conditions or changes to the conditions in the cell cultures. The control unit 107 may include applications (apps) employed for storing or conveying data (graphs, charts, etc.) or send out warning signals on the status of the culture (e.g., "dangerous levels of ammonia"). The warning signals may be audible (e.g., phone ringing or phone messaging), text messaged, emailed, etc.

The information conveyed may be simple or extremely complex and may be customized by the user.

Figure 3:
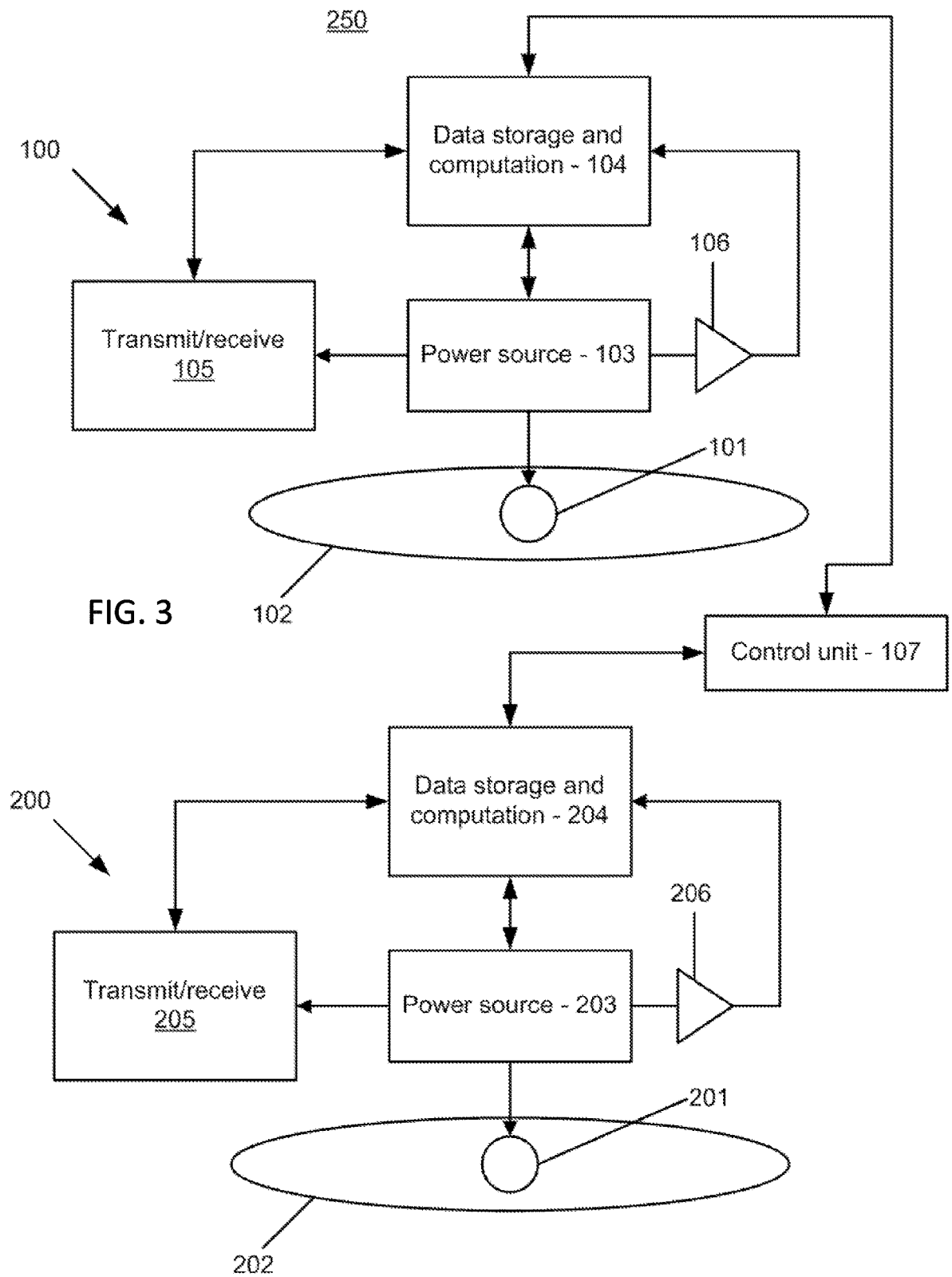
FIG. 3 is a block/flow diagram showing a device/method for monitoring electrochemical signals in a cell culture having a control unit to receive information from other components and a reference component for generating a control sample in accordance with one embodiment.

Referring to FIG. 3, a reference component 200 may be employed along with the apparatus 100 having one or more reference samples 202 in a system 250. In addition to one or more reference samples 202, the reference component 200 may be in communication with the control unit 107. The reference component 200 includes the same components as the apparatus 100 and serves as a model or control to evaluate the data from the apparatus 100. The apparatus 100 and the reference component 200, in this embodiment, may each include an amplifier 206 to boost the signals from the electrochemical sensors 101, 201, respectively. The apparatus 100 and the reference component 200 each include transmitter/receiver devices 105, 205, digital computers 104, 204, and power sources 103, 203, configured similarly to each other to monitor their respective cell cultures.

In one embodiment, the system 250 comprises one or more reference electrochemical sensors 201 positioned adjacent to a reference sample 202. A reference power source 203 is connected with the reference sensors 201 (e.g., infrared sensors and/or other sensors). A reference data storage and computation device 204 is configured to receive and analyze the infrared heat signal from the reference infrared sensors 201. A reference transmit/receive device 205 is connected with the reference storage and computation device 204 and configured to communicate information with the control unit 107.

Figure 4:
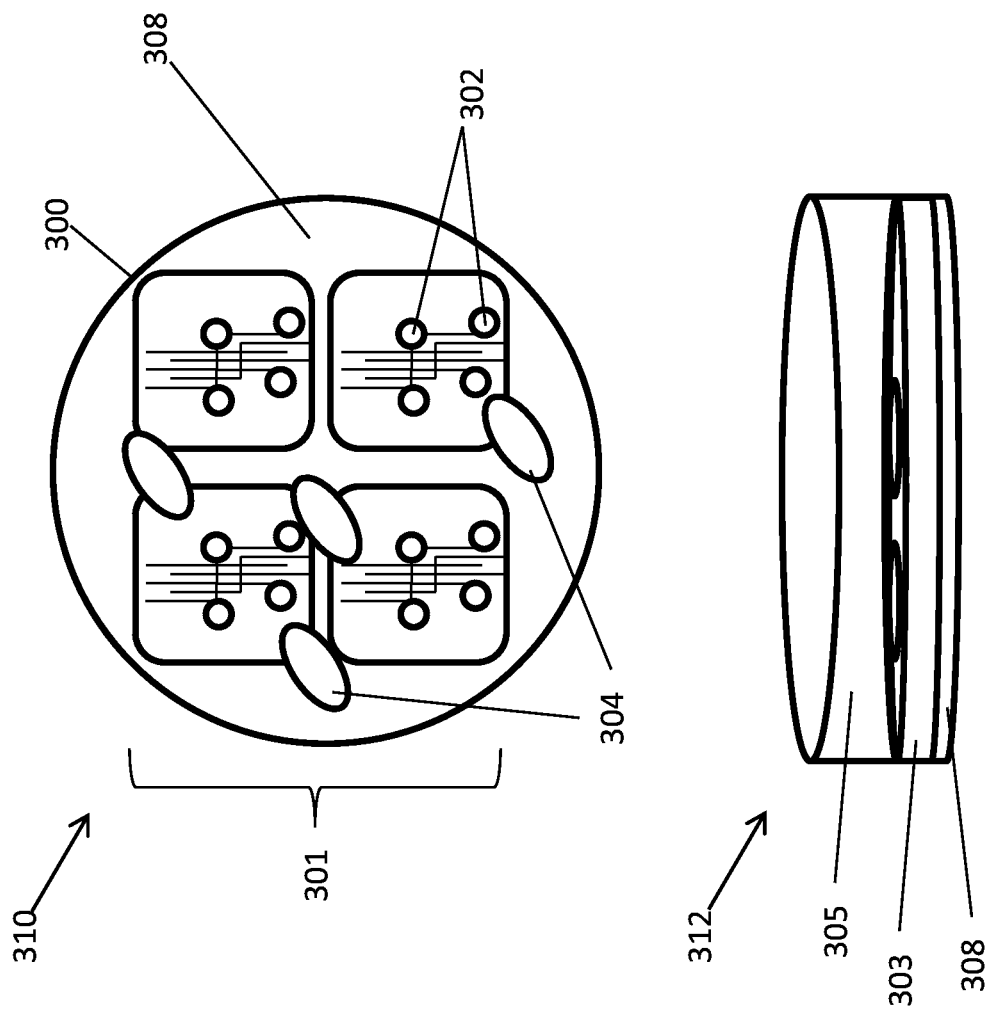
FIG. 4 is a diagram showing multiple views of a device for monitoring electrochemical signals and depicting a sensor array for monitoring a cell culture in a Petri dish in accordance with one embodiment.

Referring to FIG. 4, a device 300 for sensing cell activity is shown in accordance with another illustrative embodiment. A top view 310 of the device 300 shows a sensors array 301 and cultures 304. A side view 312 shows the device 300 is a Petri dish 305 with a culture medium 303 thereon. The device 300 includes a substrate 308 (e.g. a semiconductor wafer, ceramic, printed wiring board, plastic, glass or other suitable material) having the sensor array 301 formed thereon. The sensor array 301 may include etched metallizations to connect sensors 302 in the sensor array 301 to a power source (on-device or off-device) and data collection component. See e.g., FIG. 1. The sensor array 301 includes a plurality of individual electrochemical sensors 302 which are positionable near or embedded within the culture medium 303 and employed to monitor changes in temperature, pH, ion concentration and biomolecule concentration, etc. in a cell culture or cultures 304 grown on a Petri dish 305 or other container. An electrochemical sensor 302 may include a plurality of microsensors (302), each measuring, e.g., activity and/or size of a culture mass, e.g., in the range of micrometers, and each capable of sensing the presence and concentration of cells.

The sensors 302 and the substrate 308 may be sterile or coated with a sterile material or otherwise protected so as to not influence the cell activity in the medium 303. The sensors 302 may be positioned at regular intervals or may be distributed with different densities depending on a relative position within the Petri dish 305. Each sensor 302 includes a unique signal, an index or address or other distinguishing identifier so that the position and measurements at that position can be known and stored.

The device 300 may be submerged in the medium 303 or may be positioned over or on the medium 303. In one embodiment, the device 300 is attached to the Petri dish 305 (e.g., a disposable sticker) and provided as a unit.

Figure 5:
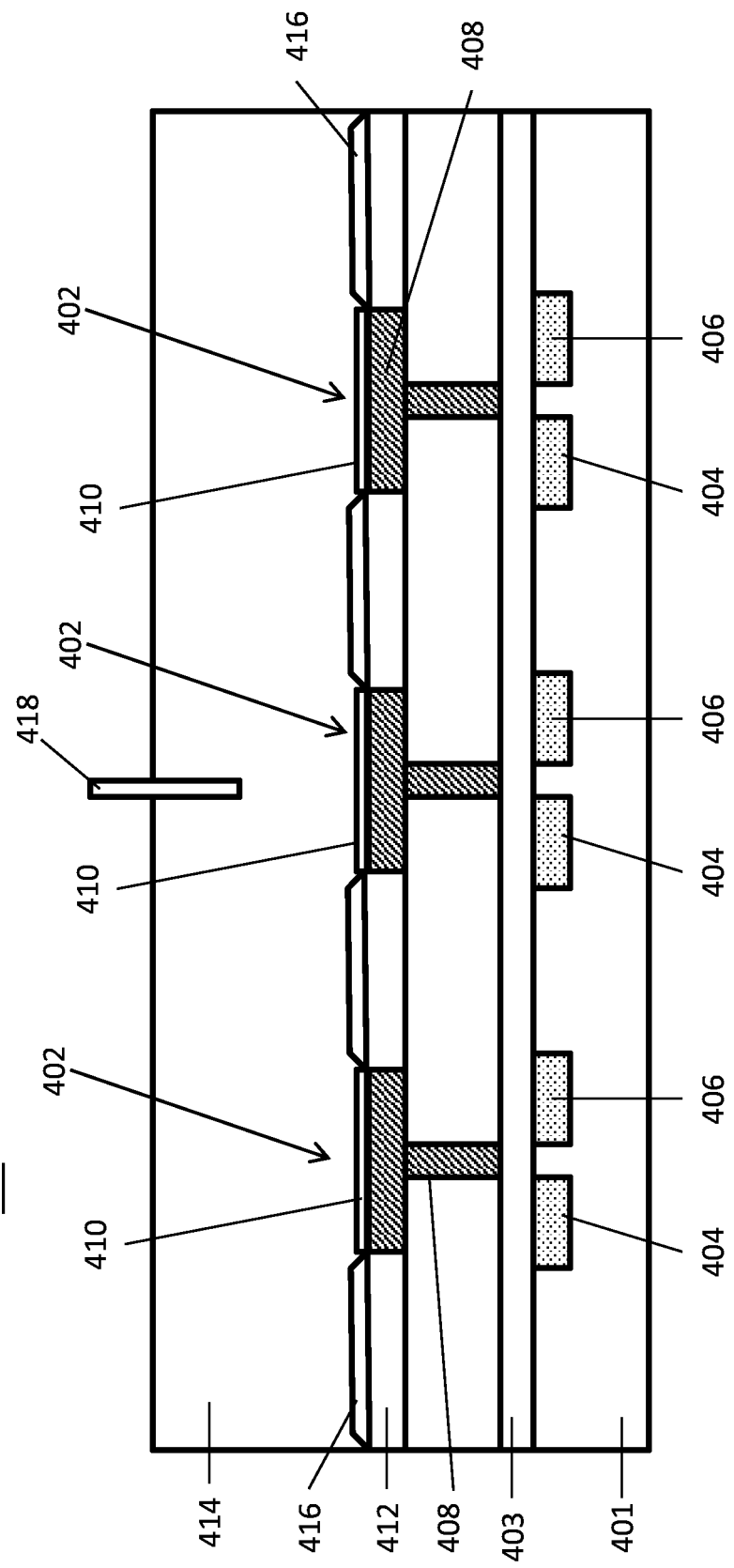
FIG. 5 is a cross-sectional view of a device for monitoring electrochemical signals and depicting a microscale electrochemical sensor in accordance with one embodiment.

Referring to FIG. 5, an electrochemical sensor device 400 is shown in accordance with one illustrative embodiment. The electrochemical sensor device 400 includes a substrate 401 (e.g., semiconductor substrate, printed wiring board, etc.). The substrate 401 includes a gate dielectric layer 403 formed thereon. The substrate 401 may include a suitable semiconductor material. In one embodiment, the substrate 401 includes a silicon based semiconductor material, e.g., Si, SiGe, SiC, etc. and the dielectric layer 403 may include a silicon oxide, a high-k dielectric or other suitable gate dielectric material. The dielectric layer 403 may be grown, transferred or deposited on the substrate 401.

Source regions 404 and drain regions 406 are formed within the substrate 401. The substrate 401 may include one or more doped wells (not shown) to permit proper transistor device operation. The source regions 404 and drain regions 406 may be formed by ion implantation, although other processes may be employed. A dielectric layer 412 is formed over the gate dielectric 404. The dielectric layer 412 may include an oxide, a nitride, an oxynitride or other suitable dielectric material. The dielectric layer 412 is patterned to form gate openings through the dielectric layer 412. The patterning process may include a lithographic patterning process to form an etch mask followed by a reactive ion etch to form the gate openings.

A gate conductor 408 is deposited in the patterned gate openings. The gate conductor 408 may include, e.g., polycrystalline or amorphous silicon, germanium, silicon germanium, a metal (e.g., tungsten, titanium, tantalum, ruthenium, zirconium, cobalt, copper, aluminum, lead, platinum, tin, silver, gold), a conducting metallic compound material (e.g., tantalum nitride, titanium nitride, tungsten silicide, tungsten nitride, ruthenium oxide, cobalt silicide, nickel silicide), carbon nanotube, conductive carbon, graphene, or any suitable combination of these materials. The conductive material may further comprise dopants that are incorporated during or after deposition.

A planarization process may be employed to planarize a top surface and remove excess material from the gate conductor 408 deposition. The gate conductor 408 may be formed using a chemical vapor deposition (CVD) process, although other suitable deposition processes may be employed. The gate conductor 408 may include a planar portion to increase surface area of electrochemical sensors 402 formed using the gate conductor 408. A sensing surface 410 is formed over the gate conductor 408 and, in particular, over a top-most planar portion of the gate conductor 408.

The sensing surface 410 may include a material suitable for contacting a surface of cells, e.g., nutrient broths, agar plates, etc. The sensing surface 410 includes a coating material having a thin layer of nutrient medium with cells growing on the medium layer. In other embodiments, cells or materials may be grown in or on solid, gel-like and liquid media, which can form the sensing surface 410.

A protection layer 416 may be formed over the dielectric layer 412 with windows opened up over the sensing surfaces 410. The protection layer 416 includes an inert material that does not have an impact on the cell cultures. In one embodiment, the protection layer 416 includes polymeric material, such as e.g., polyethelene, polycarbonate, etc.

During operation, a cell medium 414 is employed in contact with the sensing surfaces 410. The cell medium 414 may include any media known in the art, e.g., employed in Petri dishes, etc. The cell medium may be conductive or non-conductive depending on the application. A reference electrode(s) 418 is placed into the medium 414. After a cell culture is introduced into the medium 414, electrical characteristics are monitored through the medium 414 where cell activity occurs. The changes in the medium 414 due to the cell activity are monitored using a charge or potential placed on the reference electrode 418. Changes in the medium and/or due to cell activity change a voltage applied to the gate conductors 408 of the sensors 402. The changes affect the current passing between the source and drain regions 404 and 406. This is sensed by sensor circuitry formed in other parts of the substrate 401. The information is conveyed and stored, as described above.

The sensors 402 may be based on field effect transistors technology as described; however, other structures and technology types may be employed. For example field effect transistor (FET) sensors can be replaced with or work in conjunction with bipolar junction transistor (BJT) devices with a base connected to the sensing surface 410.

Electrochemical sensors 402 are capable of measuring various parameters including the concentration of ions and biomolecules (e.g., lactate, glucose), pH and electric current. These sensors 402 can be micro- and even nano-scale in size and can also be imprinted on stickers and applied to various surfaces. The very low price of sensors makes it practical to use the sensor arrays 402 as disposable products.

The sensing surfaces 410 may be adapted for different measurements and the array of sensors 402 may include one or more different types of sensors with different sensing surfaces 410 provided for different functions. For example, non-exhaustive examples for designated sensors 402 having unique sensing surface compositions for sensing surfaces 410 that are capable of specifically monitoring concentration, activity, etc. may be provided. Illustrative examples include, e.g., a TiN layer for sensing pH, a AgCl layer to detect Cl−, a gold surface and thiol chemistry for functionalization to detect proteins and miRNA, etc.

In some embodiments, the measurements for each sensor 402 include a sensing signal that is represented by a drain current. The sensing signal may be measured by applying a gate voltage at the reference electrode 418, and, in one example, a $V_{source}=-V$ and $V_{drain}=30$ mV for an nFET. Other embodiments and outputs are also contemplated.

The sensors 402 for monitoring a cell culture are positioned near to or embedded within the medium 414 of a cell culture for recording a plurality of signals from the cell culture. The sensors 402 monitor signal streams indicative of ambient conditions, cell viability, growth and metabolism in the cell culture. The signals may include pH, temperature, concentration of sodium, potassium, calcium, chloride, lactate, glucose, electric current, electric potential, etc.

In accordance with the present principles, the ability to continuously monitor cells in a culture is provided with minimal human interaction. For example, early detection of changes in a cell culture can be determined in accordance with the present principles. The time until an infection is diagnosed is reduced, and/or the time needed to determine what the most effective antibiotic would be to treat a patient is reduced. Cells may stop growing or die due to lack of nutrients, unbalanced ambient conditions or infection by viruses, phages and fungi. Early detection of impaired cell growth is an important consideration in addressing the problem causing impaired growth. For example, early detection may permit for ambient conditions to be modified before cells experience irreversible damage. Early detection of an infection affecting cells may permit for control measures to be taken to prevent spread of the infection to other cells or specimens.

Continuous monitoring of the rate of cell growth may be employed to support research related to the use of medications. When medications, change in nutrient supply, environmental changes (e.g., partial pressure of oxygen or carbon dioxide) or other interventions such as genetic modifications intended or potentially capable of cell growth or metabolism are investigated, continuous monitoring can quantify their effect on cells and provide a measure of the kinetics of their action. Impairment in cell growth or metabolic activity, or increased rate of cell growth may include adverse effects due to drugs. Continuous monitoring of cell growth may permit for better detection of such effects.

Cells are often cultured in small compartments such as wells, which are more difficult to visually inspect. Spectrometry is employed to measure cell concentration in a liquid medium, but this needs manually positioning of wells or other containers in a designated device, which are not located within the incubator. This is labor intensive, increases the risk of mistakes and requires displacement of cells from their preferred culture environment, which may have adverse effects on cell growth. Automated agar plate inoculation systems exist that perform seeding of microbiologic samples on plates and monitor their growth using a camera but these are not commonly used in the research setting due to their inflexibility and high price.

The present principles provide automated, low cost cell growth monitoring, which saves time, reduces labor associated with lab work, saves money lost due to waste of reagents and equipment, promotes the ability to get real-time results in cell-related research, and shortens time to microbiologic results that may affect patient treatment and outcomes.

Figure 6:
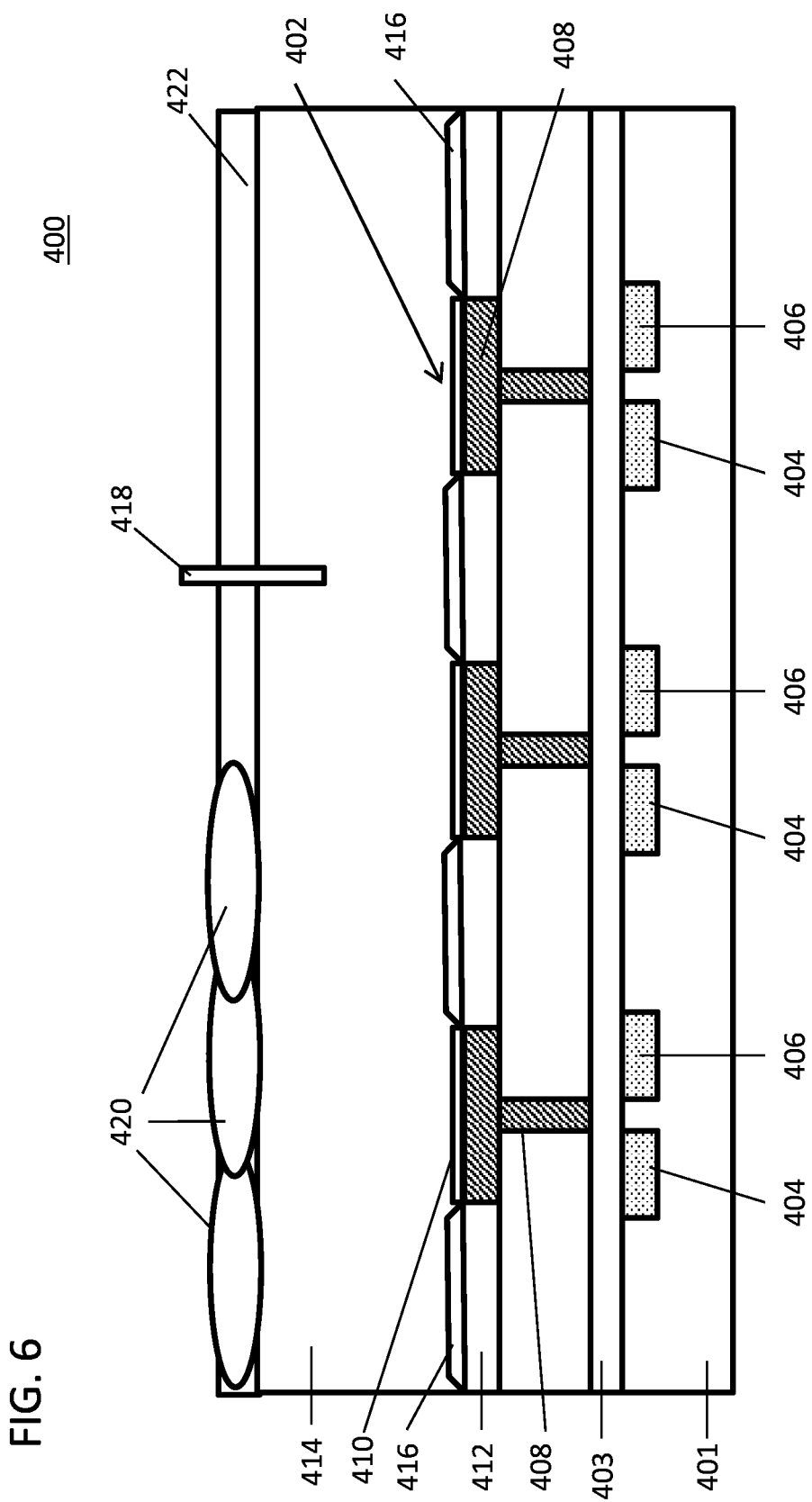
FIG. 6 is a cross-sectional view of another device for monitoring electrochemical signals including a microscale electrochemical sensor in accordance with one embodiment.

Referring to FIG. 6, the electrochemical sensor device 400 is shown in accordance with another illustrative embodiment. The sensing surface 410 may include a material suitable for contacting a surface of cells 420, e.g., nutrient broths, agar plates, etc. The sensing surface 410 includes a coating material having a thin layer of nutrient medium with cells 420 growing on the medium layer (e.g., agar) in an aqueous medium 422. In other embodiments, cells or materials may be grown in or on solid, gel-like and liquid media, which can form the sensing surface 410.

After a cell culture is introduced into the medium 414, electrical characteristics are monitored through the medium 414 where cell activity occurs. The changes in the medium 414 due to the cell activity are monitored using a charge or potential placed on the reference electrode 418. Changes in the medium and/or due to cell activity change a voltage applied to the gate conductors 408 of the sensors 402. The changes affect the current passing between the source and drain regions 404 and 406. This is sensed by sensor circuitry formed in other parts of the substrate 401. The information is conveyed and stored, as described above.

Electrochemical sensors 402 are capable of measuring various parameters including the concentration of ions and biomolecules (e.g., lactate, glucose), pH and electric current. These sensors 402 can be micro- and even nano-scale in size and can also be imprinted on stickers and applied to various surfaces. The very low price of sensors makes it practical to use the sensor arrays 402 as disposable products.

The sensing surfaces 410 may be adapted for different measurements and the array of sensors 402 may include one or more different types of sensors with different sensing surfaces 410 provided for different functions. For example, non-exhaustive examples for designated sensors 402 having unique sensing surface compositions for sensing surfaces 410 that are capable of specifically monitoring concentration, activity, etc. may be provided. Illustrative examples include, e.g., a TiN layer for sensing pH, a AgCl layer to detect Cl−, a gold surface and thiol chemistry for functionalization to detect proteins and miRNA, etc.

An array of chemical FET sensors 402 is embedded in a surface for growing cells. The pH can be sensed by making the sensing surface to be TiN, Cl− can be detected by changing the sensing surface to AgCl layer, proteins and miRNA can be detected by using gold surface and thiol chemistry for functionalization. Measurements for each sensor includes a sensing signal using the drain current. The sensing signal can be measured by applying gate voltage (Vgate) at the reference electrode 418, e.g., Vsource=0V and Vdrain=30 mV for nFETs. The sensing surface 410 can be of a planar shape or a 3-dimensional shape, e.g., a needle embedded in agar 414. Other embodiments and outputs are also contemplated.

Figure 7:
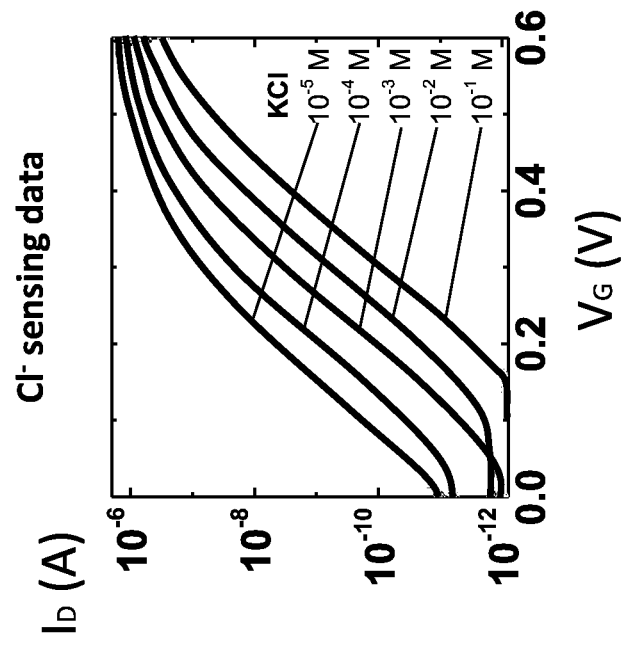
FIG. 7 is a plot showing sensitivity data for pH sensing data in accordance with one embodiment.

Referring to FIG. 7, a plot of drain current ($I_D$) in amperes is plotted against solution voltage ($V_{sol}$) in Volts to indicate a pH measurement by the sensing surfaces 410 (e.g., TiN for measuring pH) and devices 402. $V_{sol}$ here is the voltage of the reference node 418 (in FIGS. 5 and 6). The pH sensing data measured, in this example, shows plots for pH 5, pH 6 and pH 8 and provides a relationship between the pH due to cell activity and device related sensitivities ($I_D$ changes with pH changes). The change in threshold voltage ($\Delta V_T$), in this example, is 42 mV/pH.

Using this information, sensitivity data collected from the sensor 402 (FIG. 6) can be employed to correlate measurements to cell activity or status. In one example, the pH changes can be determined from electrical signals from the sensor 410 (e.g., drain current changes, threshold voltage changes, etc.).

Figure 8:
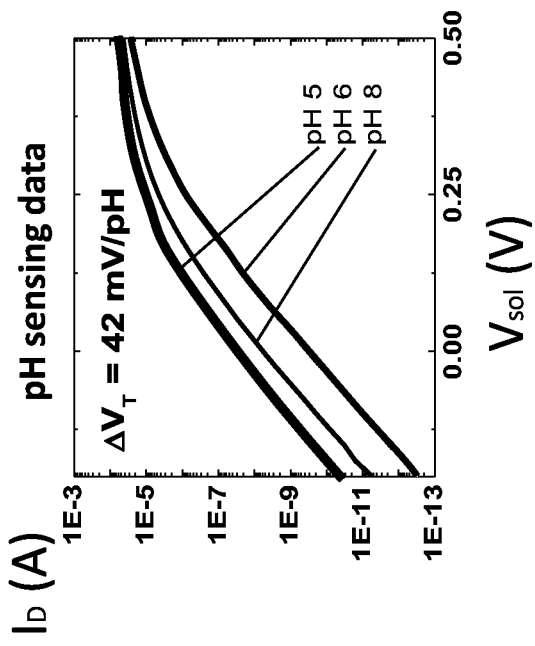
FIG. 8 is a plot showing sensitivity data for $Cl^-$ concentration sensing data in accordance with another embodiment.

Referring to FIG. 8, a plot of drain current ($I_D$) in amperes is plotted against gate voltage ($V_G$) in Volts to indicate a Cl− measurement by the sensing surfaces 410 (e.g., AgCl/Ag for measuring Cl−) and devices 402. VG here is the voltage of the reference node 418 (in FIGS. 5 and 6). The Cl− sensing data measured, in this example, shows plots for $10^{-1}$ M KCl (molarity of potassium chloride) to $10^{-5}$ M KCl and provides a relationship between the Cl− concentration due to cell activity and device related sensitivities ($I_D$ changes with Cl− concentration).

Using this information, sensitivity data collected from the sensor 402 (FIG. 6) can be employed to correlate measurements to cell activity or status. In one example, the Cl− concentration changes can be determined from electrical signals from the sensor 410 (e.g., drain current changes, etc.).

Figure 9:
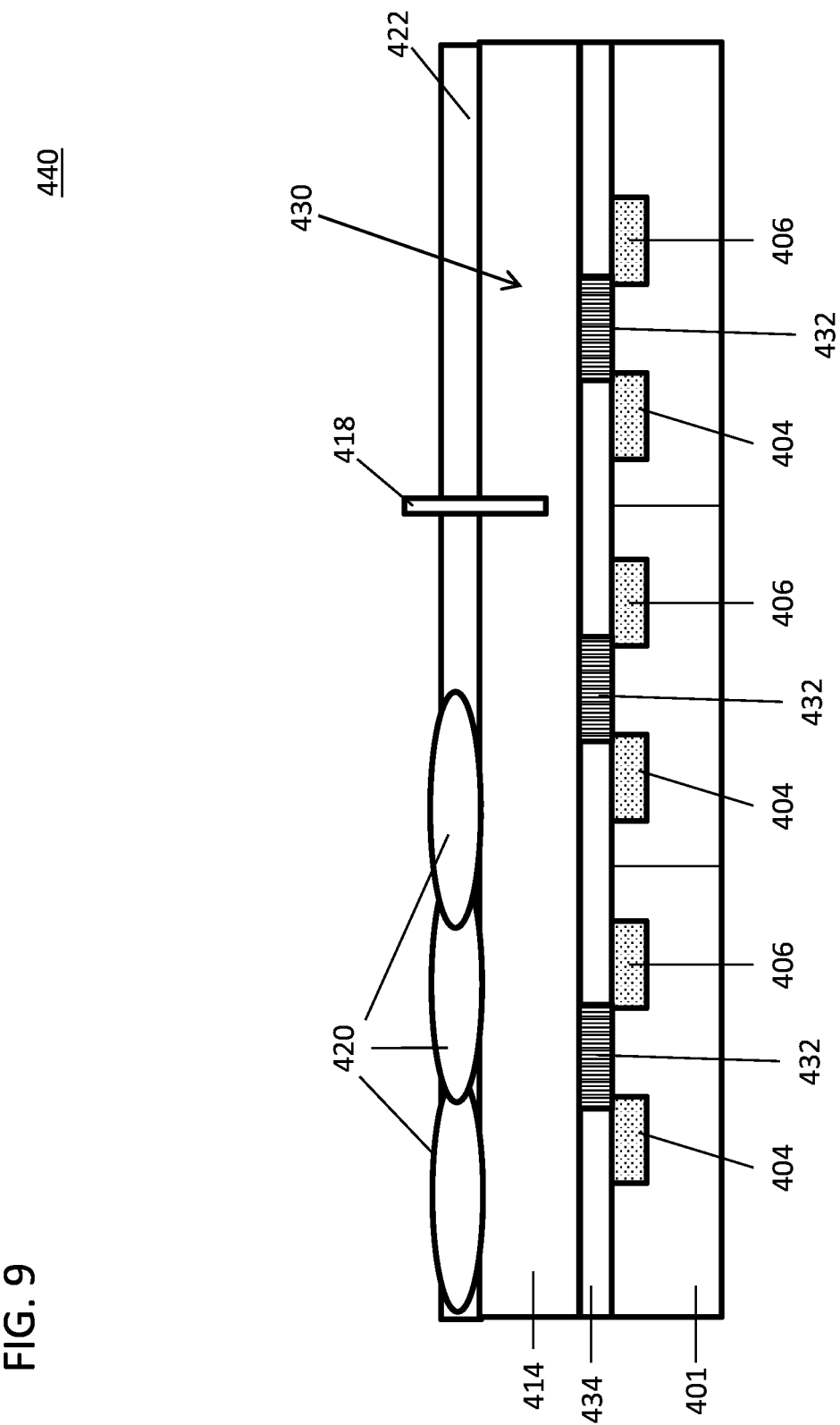
FIG. 9 is a cross-sectional view of another device for monitoring electrochemical signals including a gate dielectric as a sensing surface or having a sensing surface thereon and a medium acting as a gate conductor in accordance with one embodiment.

Referring to FIG. 9, another electrochemical sensor device 440 is shown in accordance with another illustrative embodiment. A sensing surface 432 may include a gate dielectric material suitable for contacting cells 420, e.g., through nutrient broths, agar plates, etc. The medium 414 represents the gate conductor in this structure and the medium 414 is in contact with the gate dielectric or sensing surface 432 (e.g., formed on or of the gate dielectric material).

The sensing surface 432 can include a dielectric material such as, e.g., $HfO_2$, $Al_2O_3$, $SiO_2$, a dual layer of $SiO_2/HfO_2$, $SiO_2/Al_2O_3$, or other suitable gate dielectric material. The gate dielectric 432 can be formed in a dielectric layer 434 (e.g., $SiO_2$). The gate dielectric 432 used as is (exposed to agar 414 or cells 420) or an additional bio-layer may be deposited on top of the gate dielectric to specifically bind target bio-molecules to form the sensing surface 432. For each sensor 430, a sensing signal can include the drain current. In one embodiment, the sensing signal is measured by applying gate voltage (Vgate) at the reference electrode 418. In one example, when Vsource=0V, Vdrain~30 mV for nFETs.

After a cell culture is introduced into the medium 414, electrical characteristics are monitored through the medium 414 where cell activity occurs. The changes in the medium 414 due to the cell activity are monitored using a charge or potential placed on the reference electrode 418. Changes in the medium and/or due to cell activity change a voltage applied to the gate conductors 432 of the sensors 430. The changes affect the current passing between the source and drain regions 404 and 406. This is sensed by sensor circuitry formed in other parts of the substrate 401. The information is conveyed and stored, as described above.

Electrochemical sensors 430 are capable of measuring various parameters including the concentration of ions and biomolecules (e.g., lactate, glucose), pH and electric current. These sensors 430 can be micro- and even nano-scale in size and can also be imprinted on stickers and applied to various surfaces. The very low price of sensors makes it practical to use the sensor arrays 430 as disposable products.

The sensing surfaces 432 may be adapted for different measurements and the array of sensors 430 may include one or more different types of sensors with different sensing surfaces 432 provided for different functions. For example, non-exhaustive examples for designated sensors 430 having unique sensing surface compositions for sensing surfaces 432 that are capable of specifically monitoring concentration, activity, etc. may be provided. While the gate dielectric can be the sensing surface, the sensing surface may be treated, textured or coated in accordance with specific applications or measurments. In one embodiment, the sensing layer includes a gate dielectric, and the gate conductor includes the medium being measured. Other embodiments and outputs are also contemplated.

Figure 10:
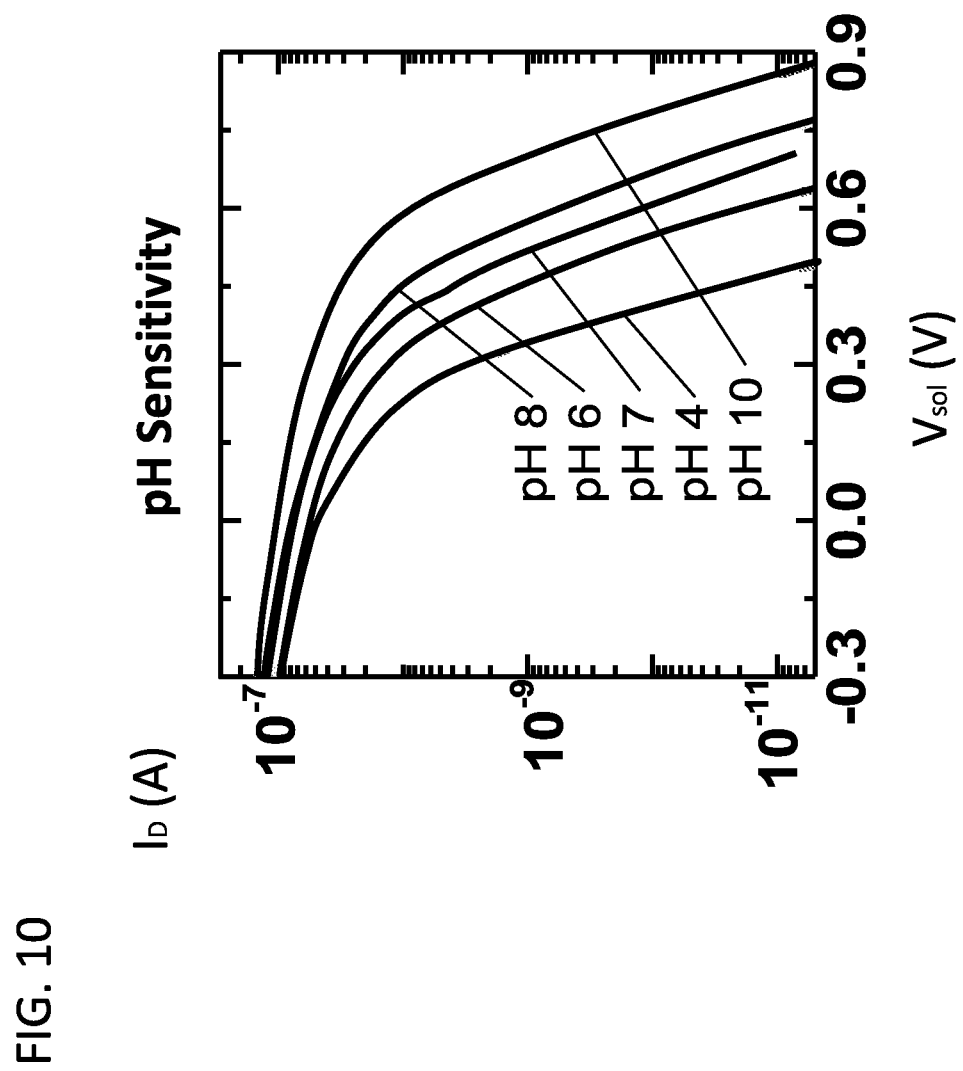
FIG. 10 is a plot showing sensitivity data for pH sensing data in accordance with one embodiment.

Referring to FIG. 10, a plot of drain current ($I_d$) in amperes is plotted against solution voltage ($V_{sol}$) in Volts to indicate a pH measurement by the sensing surfaces 432 (e.g., $HfO_2$ gate dielectric for measuring pH) and devices 430. $V_{sol}$ here is the voltage of the reference node 418 (in FIG. 9). The pH sensing data measured, in this example, shows plots for pH 5, pH 6, pH 7, pH 8 and pH 10 and provides a relationship between the pH due to cell activity and device related sensitivities ($I_d$ changes with pH changes).

Figure 11:
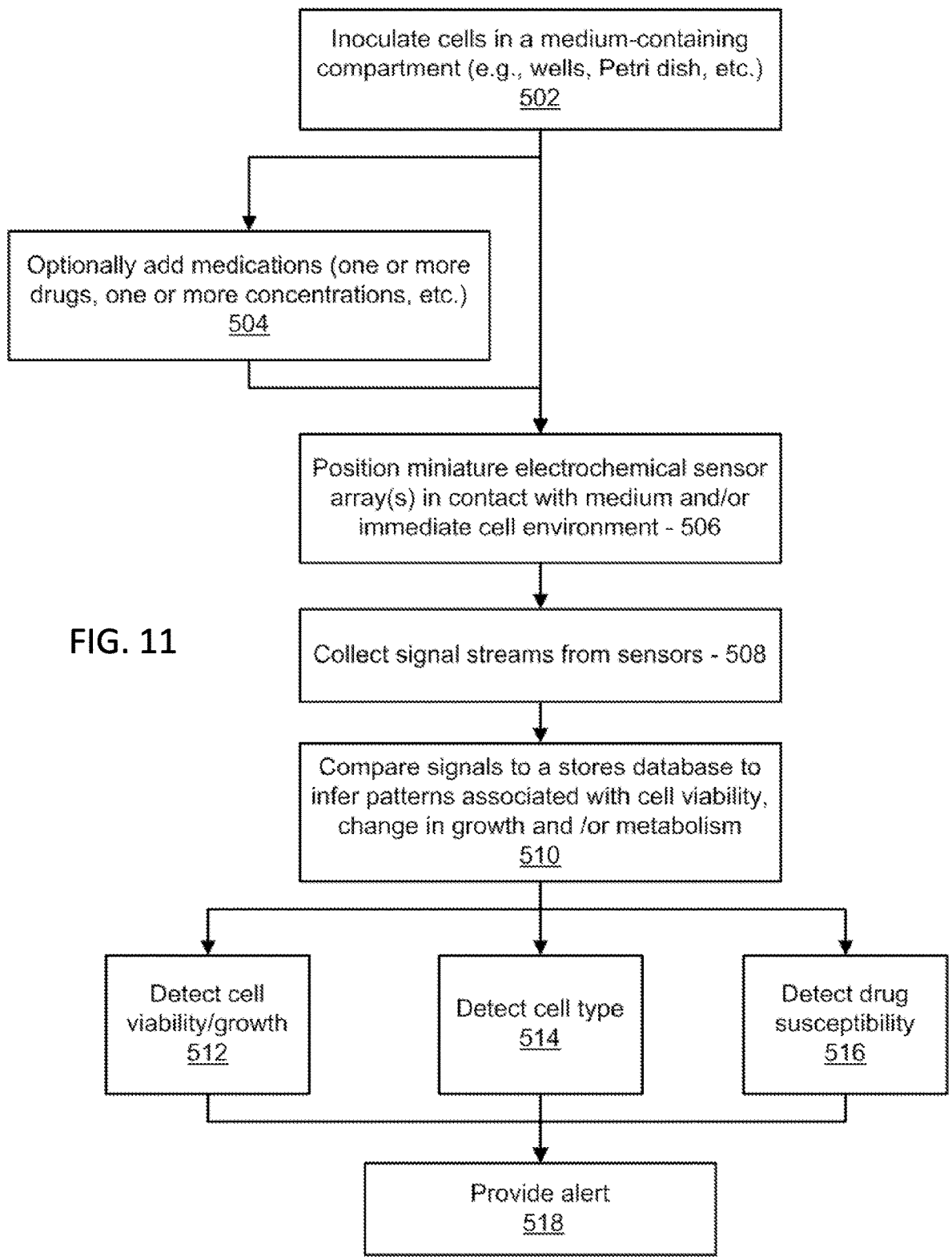
FIG. 11 is a block/flow diagram showing a system/method for monitoring a cell culture in accordance with the present principles.

Referring to FIG. 11, an illustrative method is shown for monitoring a cell culture in accordance with the present principles. In block 502, cells are placed (inoculated) into a cell medium, e.g., a Petri dish, well or container. Depending on the measurements to be applied tested or made, in block 504, one or more drugs or concentrations of drugs are administered to the cell culture. This is optional depending on the type of cell culture and the effects being tested or measured. In block 506, an electrochemical sensor array is provided. The sensor array may have been present in the container prior to adding the cell medium (e.g., a sticker placed in a Petri dish). The sensor array may be placed on top of, near to or in contact with a surface of the cell medium.

In block 508, signal streams are collected from the sensors. This may include monitoring drain currents or monitoring other electrical characteristics. In block 510, the signals may be compared to stored data, to control groups, to other portions of the cell culture. Patterns and other information can be inferred for cell viability, change in growth and metabolism, among other things.

Blocks 512, 514 and 516 provide a response to the signals received from the sensors. The response depends on the application of the device. For example, in block 516, drug susceptibility is detected using the changes measured by the sensors. The drug susceptibility is only measured if drugs are optionally administered in block 504. In block 514, cell types may be detected. This may include determining cancer cells versus normal cells, resistant cells versus non-resistant, etc. In block 512, cell viability or growth is measured or detected. In block 518, based on the results obtained in blocks 512, 514 and 516, an alert is provided to a user regarding the status or activity of the cell culture. The alert may be simple (e.g., an alarm) or complex depending on how the system is set up. In one embodiment, a look up table may be stored that indexes conditions with messages that may be employed for sending an alert message to a user. The message may be sent to/from a phone, etc.

Having described preferred embodiments for electrochemical sensors for cell culture monitoring (which are intended to be illustrative and not limiting), it is noted that modifications and variations can be made by persons skilled in the art in light of the above teachings. It is therefore to be understood that changes may be made in the particular embodiments disclosed which are within the scope of the invention as outlined by the appended claims. Having thus described aspects of the invention, with the details and particularity required by the patent laws, what is claimed and desired protected by Letters Patent is set forth in the appended claims.

What is claimed is:

1. A device for monitoring a cell culture, comprising:
   one or more electrochemical sensors configured to be positioned adjacent to or-embedded within a medium of a cell culture, a sensing surface of the one or more electrochemical sensors formed directly on a surface of a gate conductor and configured to generate signals in accordance with cell activity at a region of the cell culture proximate to the gate conductor of the one or more electrochemical sensors;
   a data storage device configured to receive and store the signals from the one or more electrochemical sensors; and
   a computation device configured to analyze the signals from the one or more electrochemical sensors to determine cell activity over time using sensitivity information.

2. The device as recited in claim 1, wherein the data storage device and the computation device are included in a same device and the same device is selected from the group consisting of a smartphone and a computer.

3. The device as recited in claim 1, further comprising a transmit device coupled to the one or more electrochemical sensors to communicate with at least the computation device.

4. The device as recited in claim 1, wherein the signals indicate at least one of ambient conditions, cell viability, growth and metabolism in the cell culture.

5. The device as recited in claim 1, wherein the signals represent parameters selected from the group consisting of: pH, temperature, material concentrations, electric current and electric potential.

6. The device as recited in claim 5, wherein the material concentrations are selected from the group consisting of: sodium, potassium, calcium, chloride, lactate and glucose.

7. The device as recited in claim 1, further comprising a reference component including an electrochemical sensor array to enable a comparison to the one or more electrochemical sensors.

8. The device as recited in claim 1, wherein the device is disposable.

9. The device as recited in claim 1, wherein the one or more electrochemical sensors include transistor devices having a sensing layer formed on a contact of the transistor devices.

10. The device as recited in claim 1, wherein the computation device is further configured to compare the signals from different regions of the cell culture.

* * * * *